(12) United States Patent
Sharma et al.

(10) Patent No.: US 7,625,868 B2
(45) Date of Patent: Dec. 1, 2009

(54) METHODS AND COMPOSITIONS FOR INHIBITING ANGIOGENESIS

(75) Inventors: Mahesh C. Sharma, Turnersville, NJ (US); George P. Tuszynski, Pittsgrove, NJ (US)

(73) Assignee: Philadelphia, Health and Education Corporation, Philadelphia, PA (US)

( * ) Notice: Subject to any disclaimer, the term of this patent is extended or adjusted under 35 U.S.C. 154(b) by 149 days.

(21) Appl. No.: 11/650,393

(22) Filed: Jan. 5, 2007

(65) Prior Publication Data

US 2007/0128196 A1 Jun. 7, 2007

Related U.S. Application Data

(62) Division of application No. 10/363,328, filed as application No. PCT/US01/27310 on Sep. 4, 2001, now Pat. No. 7,160,858.

(60) Provisional application No. 60/277,204, filed on Mar. 20, 2001, provisional application No. 60/229,667, filed on Sep. 1, 2000.

(51) Int. Cl.
*A61K 39/395* (2006.01)

(52) U.S. Cl. .................... 514/12; 424/130.1; 424/138.1; 424/141.1; 424/158.1

(58) Field of Classification Search .................... 514/12; 424/130.1, 138.1, 141.1, 155.1
See application file for complete search history.

(56) References Cited

U.S. PATENT DOCUMENTS

| 5,051,364 A | 9/1991 | Isacke et al. | 435/240.27 |
| 5,792,845 A | 8/1998 | O'Reilly et al. | 536/23.1 |

FOREIGN PATENT DOCUMENTS

| WO | WO 98/54217 | 3/1998 |
| WO | WO 99/48916 | 9/1999 |
| WO | WO 00/11033 | 2/2000 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Jain (Scientific American Jul. 1994).*
MSNBC News Services, "Mixed results on new cancer drug", Nov. 9, 2000.*
Gura (Science, v278, 1997, pp. 1041-1042).*
Sim et al. (Cancer Research, vol. 57, 1997).*
Aarli et al., "Inhibition of phytohaemagglutinin-induced lymphoproliferation by soluble annexin II in sera from patients with renal cell carcinoma", APMIS 1997 105:699-704.
Chung et al., "Cell Surface Annexin II Is a High Affinity Receptor for the Alternatively Spliced Segment of Tenascin-C", J. Cell Biol. 1994 126:539-548.
Sim et al., "A Recombinant Human Angiostatin Protein Inhibits Experimental Primary and Metastatic Cancer[1]", Cancer Research 1997 57:1329-1334.
Moser et al., "Angiostatin binds ATP synthase on the surface of human endothelial cells", Proc. Natl. Acad. Sci. USA 1999 96:2811-2816.
Ulvestad et al., "Identification of a soluble Fcγ-binding molecule (annexin II) in human serum using a competitive ELISA", APMIS 1994 102:667-673.
Archarya et al., "Annexin II:Potential Role in Plasmin-Mediated Invasion of Malignant Glioma Cells", Blood 1998 92(10) Suppl. 1 Part 1-2:42a XP009024406.
Balch et al., "Annexins II and V Inhibit Cell Migration", Experimental Cell Research 1997 237:259-263 XP-002268193.
Hajjar et al., "Annexin II and Regulation of Cell Surface Fibrinolysis", Annals of the New York Academy of Sciences 2000 265-271 XP009024460.
Hajjar et al., "New Concepts in Fibrinolysis and Angiogenesis", Current Atherosclerosis Reports 2000 2:417-421 XP009024206.
O'Reilly et al., "Angiostatin:A Novel Angiogenesis Inhibitor That Mediates the Suppression of Metastases by a Lewis Lung Carcinoma", Cell 1994 79:315-328 XP002015254.
Siever et al., "Molecules in Focus—Extracellular Annexin II", Int. J. Biochem. Cell Biol. 1997 29(11) :1219-1223 XP-002268192.

* cited by examiner

*Primary Examiner*—Brandon J Fetterolf
(74) *Attorney, Agent, or Firm*—Licata & Tyrrell P.C.

(57) ABSTRACT

Methods for inhibiting angiogenesis in endothelial cells and selectively inducing apoptosis in endothelial cells via compounds which binds annexin II are provided. These compounds and methods for using these compounds are useful in the treatment of diseases or disorders characterized by unwanted angiogenesis. Also provided are pharmaceutical compositions containing a compound which binds annexin II and a pharmaceutically acceptable vehicle and methods for identifying such compounds.

1 Claim, No Drawings

SEQUENCE LISTING

```
<160> NUMBER OF SEQ ID NOS: 4

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic

<400> SEQUENCE: 1

Ser Leu Tyr Tyr Tyr Ile Gln Gln Asp Thr Lys
 1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
```

-continued

```
<400> SEQUENCE: 2

Ser Tyr Ser Pro Tyr Asp Met Leu Glu Ser Ile Lys
  1               5                  10

<210> SEQ ID NO 3
<211> LENGTH: 10
<212> TYPE: PRT
<213> ORGANISM: Artificial Sequence
<220> FEATURE:
<221> NAME/KEY: MISC_FEATURE
<222> LOCATION: 6
<223> OTHER INFORMATION: X=any amino acid
<220> FEATURE:
<223> OTHER INFORMATION: Description of Artificial Sequence: Synthetic

<400> SEQUENCE: 3

Ala Leu Leu Tyr Leu Xaa Gly Gly Asp Asp
  1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 4

Tyr Leu Ser Glu Lys Lys Gly Gly Asn Gly Lys Asn
  1               5                  10
```

METHODS AND COMPOSITIONS FOR INHIBITING ANGIOGENESIS

INTRODUCTION

This patent application is a divisional of U.S. patent application Ser. No. 10/363,328, filed May 9, 2003, now U.S. Pat. No. 7,160,858, which is the National Phase of PCT Application Serial No. PCT/US2001/27310, filed Sep. 4, 2001, which claims the benefit of priority from U.S. Provisional Application Ser. No. 60/277,204, filed Mar. 20, 2001 and U.S. Provisional Application Ser. No. 60/229,667, filed Sep. 1, 2000.

BACKGROUND OF THE INVENTION

There is extensive evidence demonstrating that angiogenesis, the process of new blood vessel growth, is essential for the growth of solid tumors and their metastases. Blood capillaries are primarily composed of endothelial cells which are usually quiescent under normal physiological conditions. In response to external stimuli, quiescent endothelial cells can degrade the basement membrane via extracellular matrix proteases that permit the endothelial cell to extravasate, and to invade the stromal space and basement membrane. These cells are then capable of changing their morphology, proliferating and forming neovessels (Folkman, J. and Y. Shing. 1992. *J. Biol. Chem.* 267:10931-10934). To stimulate angiogenesis, tumors induce a variety of factors, including fibroblast growth factor (bFGF) and vascular endothelial growth factor (VEGF). Many malignant tumors, however, also generate inhibitors of angiogenesis, including angiostatin and endostatin (O'Reilly, M. S. et al. 1994. *Cell* 79:315-328; O'Reilly, M. S. et al. 1997. *Cell* 88:277-285). This complex process implies the presence of multiple controls which can be turned on and off within a short period of time to regulate the angiogenic process.

The process of angiogenesis is tightly regulated by both negative and positive feedback control factors and the result is a homeostatic condition. Imbalance of these factors under pathological conditions can lead to development and progression of disease processes such as tumor growth, diabetic retinopathy, tissue and organ malfunction, and cardiovascular disorders (Folkman, J. 1995. *Nat. Med.* 1:27-31). Angiostatin is a powerful negative regulator of angiogenesis and potentially can inhibit the growth of primary tumors and metastases in mice (Sim, B. K. et al. 1997. *Cancer Res.* 57:1329-1334).

Angiostatin was purified from the urine of mice bearing a Lewis lung carcinoma and was identified as a 38 kDa internal fragment of plasminogen (amino acids 98-440) that constituted the first four kringle's of the molecule. Angiostatin can also be generated in vitro by limited proteolysis of plasminogen. Angiostatin produced by various methods has been shown to regress tumor growth in mice (Gately, S. et al. 1997. *Proc. Natl. Acad. Sci. USA* 94:10868-10872; Gately, S. et al. 1996. *Cancer Res.* 56:4887-4890; Stathakis, P. et al. 1997. *J. Biol. Chem.* 272:20641-20645; Dong, Z. et al. 1997. *Cell* 88:801-810). When tested in vitro, angiostatin has been shown to inhibit cell proliferation, migration, and three-dimensional capillary tube formation in collagen gels, all of which are essential steps in angiogenesis. In vivo, angiostatin is generated by hydrolysis of plasminogen with a number of enzymes including metalloproteinase from macrophages, plasmin reductase, MMP-7 (matrix metalloproteinase 7), gelatinase B/type IV collagenases, MMP-9 (matrix metalloproteinase 9), and pancreatic elastase. Angiostatin has also been shown to efficiently inhibit growth of a broad spectrum of murine and human tumor models in mice (O'Reilly, M. S. et al. 1996. *Nat. Med.* 2:689-692; O'Reilly, M. S. et al. 1994. *Cold Spring Harbor Symp. Quant. Biol.* 59:471-482; Wu, Z. et al. 1997. *Biochem. Biophys. Res. Commun.* 236:651-654; Griscelli, F. et al. 1998. *Proc. Natl. Acad. Sci. USA* 95:6367-6372) by inhibiting the neovascularization of the tumor, while plasminogen itself failed to inhibit angiogenesis and tumor regression. These data indicate that the specific conformation of the kringle domain is important for angiostatin's anti-angiogenic activity.

Despite its potent anti-cancer value, however, the mechanism of angiostatin's actions and the identity of its cellular receptor are not well defined.

Annexin II is one of the most abundant endothelial cell fibrinolytic receptors for plasminogen and plasminogen activator (Hajjar, K. A. et al. 1994. *J. Biol. Chem.* 269:21191-21197; Kang, H. M. et al. 1999. *Trends Cardiovasc. Med.* 9:92-102). Annexin II organizes the assembly of tissue plasminogen activator and plasminogen on its surface. This trimolecular assembly on endothelial cells can produce plasmin at maximum efficiency in the vascular bed (Hajjar, K. A. et al. 1994. *J. Biol. Chem.* 269:21191-21197; Felez, J. et al. 1996. *Thromb. Haemost.* 76:577-584; Kassam, G. et al. 1998. *Biochemistry* 37:16958-16966). This cell surface-produced plasmin is protected from inactivation. Plasmin is a broad spectrum trypsin-like serine protease that degrades fibrin and several endothelial cell matrix proteins like laminin, thrombospondin, and collagens. The proteolytic degradation of extracellular matrix and dissolution of basement membrane is necessary for endothelial and tumor cells to invade, migrate and promote angiogenesis and metastasis (Kang, H. M. et al. 1999. *Trends Cardiovasc. Med.* 9:92-102).

SUMMARY OF THE INVENTION

The present invention provides methods for identifying and using compositions which inhibit angiogenesis via their interaction with annexin II and/or angiostatin. These methods are based on the identification of annexin II as a specific, high affinity angiostatin binding receptor. Compounds capable of inhibiting angiogenesis can now be identified by examining their ability to bind to annexin II. Preferred inhibitors of angiogenesis compete with angiostatin to bind with annexin II. Modulators of the interaction of angiostatin and annexin, particularly agents which compete with or mimic angiostatin binding to annexin II, are believed to inhibit angiogenesis by promoting endothelial cell apoptotic activity.

DETAILED DESCRIPTION OF THE INVENTION

An angiostatin-specific receptor has now been identified and purified from endothelial cells. The receptor is a 35 kDa protein that is identical in sequence to annexin II, a known plasminogen receptor. The binding of angiostatin to this receptor in endothelial cells has been shown to be both specific and high affinity. Identification of this angiostatin receptor in cells provides a mechanism which can be exploited for identification of novel inhibitors of angiogenesis as well as a method of regulating angiogenesis in cells.

Angiostatin was generated by limited proteolytic digestion of human plasminogen using purified bovine pancreatic elastase. The protein was purified in a single step by lysine-sepharose affinity chromatography to almost 95% homogeneity as determined by SDS-PAGE. The homogeneous fraction was pooled, concentrated, dialyzed and filter sterilized. The purified fraction was then further characterized for immunoreactivity with anti-Kringle 1-3 (K1-3) monoclonal antibody. Purified angiostatin strongly immuno-reacted with structure-specific anti-K1-3 monoclonal antibody. To demonstrate even further that the purified protein was angiostatin, the 38 kDa band was transferred to a PVDF membrane and stained with amido black. The stained band was cut out from the membrane and N-terminal sequencing performed. An amino acid sequence of YLSEKKGGNGKN (SEQ ID NO:4) was generated which is homologous to the published sequence of angiostatin (K1-4). A search of the Swiss Protein database indicated that the sequences matched only the kringle 1-4 portion of plasminogen. The angiostatin purified was then found to be active as previously reported for endothelial cell proliferation, in the same concentration ranges (O'Reilly, M. S. et al. 1994. *Cell* 79:315-328). This highly purified and bioactive angiostatin was used in subsequent experiments to identify an angiostatin binding protein, or angiostatin receptor.

Immunocytochemistry was performed on cultured bovine aortic endothelial cells in a 4 chambered tissue culture slide. Cells were fixed and permeabilized with 95% ethanol and incubated with either anti-K1-3 monoclonal antibody or HRP-conjugated secondary antibody considered as control. The test chamber was incubated with angiostatin followed by anti-K1-3 monoclonal antibody and secondary antibody. There was specific staining of endothelial cells only, while controls without addition of angiostatin or primary antibody did not stain.

To determine if cultured endothelial cells bound angiostatin through annexin II, endothelial cell lysates were tested for angiostatin binding using ligand blotting. BAEC were grown to 90& confluency. Cells were harvested and the pellet washed and resuspended in PBS. Cells were sonicated and the insoluble portion, which represented the total cell membrane fraction, was analyzed on SDS-PAGE and transferred to nitrocellulose. The membrane was blocked with 5% nonfat dry milk and then incubated with purified angiostatin (1 µg/ml) for one hour. The membrane was washed and re-incubated with anti-K1-3 antibody (1:100) for one hour followed by HRP-conjugated mouse IgG and developed by ECL. Ligand immunoblotting identified a single protein band having a molecular weight of approximately 35 kDa, consistent with that of annexin II. A parallel control immunoblot was also performed which was treated as above except for addition of angiostatin; the control blot did not exhibit any binding.

To evaluate the subcellular localization of angiostatin binding protein, the subcellular organelles of the endothelial cells were fractionated and approximately 10 micrograms of protein was resolved on 12% SDS-PAGE and subjected to ligand blot analysis. This ligand blot analysis localized the 35 kDa angiostatin binding protein to the microsomal membrane fraction. The control blot again showed no binding.

Experiments were then performed to purify the angiostatin binding protein. A progressive purification procedure was used with column chromatography. A single major band was isolated from the angiostatin affinity chromatographic procedure which had a molecular weight of 35 kDa. Angiostatin binding of these fractions was further determined by ligand blot analysis. Purified fractions were separated on 12% SDS-PAGE in two different gels and subjected to ligand blot analysis. One blot was not incubated with angiostatin and served as the control. The second test blot was then incubated with angiostatin at 1 µg/ml. Only the second test blot showed binding with angiostatin. The control was free of angiostatin binding.

Tryptic fragments of purified protein yielded the sequence SLYYYIQQDTK (SEQ ID NO:1), SYSPYDMLESIK (SEQ ID NO:2), and ALLYLXGGDD (SEQ ID NO:3), which were 100% identical with amino acids 314-324, 234-245, and 330-339, respectively, of the 339 residues of annexin II. Based on the amino acid sequence results, the 35 kDa angiostatin binding protein was identified as annexin II.

To determine the specificity of annexin II binding, cell lysates from the BAEC, NIH3T3, HUVEC, and A431 were prepared and about 10 micrograms of protein was subjected to ligand blot analysis. The binding of angiostatin was demonstrated to be limited to endothelial cells. Angiostatin bound annexin II in the BAEC and HUVEC lines, while little or no angiostatin binding was detected in A431 cells or fibroblasts. These results were confirmed by Western blot analysis using anti-annexin II monoclonal antibody. The annexin II antibody recognizes the same protein band observed in the ligand blot experiments, whereas fibroblasts showed no binding of the annexin II antigen. A431 cells showed low binding and low annexin II expression. These experiments indicated that annexin II functions as a receptor for angiostatin.

Addition of radiolabeled angiostatin to annexin II immobilized on microtiter plates demonstrated a high affinity specific binding interaction. Binding was inhibited almost 80% and 55% with unlabeled angiostatin and anti-annexin II antibody, respectively, showing the specificity of the binding between angiostatin and its receptor, annexin II. BSA was used as the control and showed negligible binding. The angiostatin/annexin II interaction was shown to be lysine-binding site dependent by ligand immunoprecipitation using anti-annexin II monoclonal antibody. When angiostatin was incubated with annexin II in the presence of 100 mM ε-ACA, binding or angiostatin was completely blocked, indicating that the binding was lysine dependent.

To further characterize the angiostatin, plasminogen and annexin II interactions, the binding of angiostatin to annexin II on a Protein A Sepharose gel was analyzed. Annexin II and anti-annexin II antibody complex was immobilized on Protein A Sepharose gel and incubated with increasing concentrations of radiolabeled angiostatin or plasminogen. The binding of angiostatin or plasminogen was concentration dependent and saturable with an apparent $K_d$ of 164 nM and 101 nM, respectively. In control experiments there was a maximum 5 to 10 percent binding to gel of radiolabeled angiostatin over the same range of concentrations, with no protein binding detected. To further characterize the binding of angiostatin to its receptor, annexin II, bound radioactive angiostatin was eluted and its identity was confirmed by SDS-PAGE followed by autoradiography. Specificity of angiostatin and annexin II binding was further demonstrated by showing that a 100-fold molar excess of unlabeled angiostatin inhibited about 80% of the radiolabeled binding. These data showed that angiostatin and plasminogen interacted with annexin II with high affinity and specificity.

The binding of radiolabeled angiostatin and plasminogen to endothelial cells was also determined. The binding of both angiostatin and plasminogen was concentration dependent and saturable with a $K_d$ of 83 nM and 125 nM, respectively. The $K_d$ value obtained for the in vivo binding experiment was within a factor of 2 of the in vitro value, suggesting that angiostatin binds annexin II on the endothelial surface.

To further demonstrate that annexin II is the receptor for angiostatin on endothelial cells, the effect of anti-annexin II monoclonal antibody on angiostatin and plasminogen binding to endothelial cells was examined. Anti-annexin II monoclonal antibody inhibited the binding of angiostatin and plasminogen by 68% and 62%, respectively. Both excess unlabeled ligands competed with others binding, demonstrating the specificity of the binding reaction. These results supported the conclusion that annexin II is the receptor for angiostatin and plasminogen on endothelial cells.

The functional significance of the angiostatin-annexin II interaction was established in experiments wherein the endothelial cell apoptotic activity of angiostatin was blocked with anti-annexin II antibodies. Anti-annexin II antibodies were found to mimic the effect of angiostatin on cell viability in a dose-dependent manner. Antibody-mediated cell death was observed with a monoclonal against the core region of annexin 11 as well as a polyclonal antibody prepared against the whole molecule. Further, immune IgG had no effect, thus indicating that the antibody mediated apoptotic activity was specific. Accordingly, these results indicate that targeted binding of annexin II with angiostatin or anti-annexin II antibodies signals cell death.

The functional consequence of angiostatin-annexin II interaction was further probed with purified angiostatin incubated with purified annexin II. The endothelial cell apoptotic activity of the resulting annexin II bound angiostatin was then examined. Its was found that the purified annexin II receptor completely abrogated the apoptotic activity of angiostatin. Consistent with the angiostatin receptor function of annexin II, was the additional finding that treatment of BAEC with excess of lys-plasminogen, which has been shown to compete for binding of angiostatin to BAEC, completely inhibited the activity of angiostatin.

Anti-annexin II monoclonal antibody was also demonstrated to inhibit tumor growth in vivo. In these experiments, anti-tumor activity was assessed in mice implanted subcutaneously with Lewis lung carcinoma (O'Reilly et al. Cell 1994 79:315-28). Tumor growth in this animal model is highly dependent upon angiogenesis. Ten mice were subcutaneously injected in the flank with $10^6$ Lewis lung carcinoma cells. After 9 days when a palpable tumor developed, mice were divided into two groups, 5 animals per group. One group of mice was treated with a single dose of anti-annexin II monoclonal antibody diluted in phosphate buffered saline (60 µg/ml of blood volume) administered intravenously. The other group, referred to herein as control animals, was treated with phosphate buffered saline alone. Relative tumor volume measured as length×width$^2$/2 was assessed in mice prior to treatment. Mice were then treated for 7 days and sacrificed. In animals treated with anti-annexin II monoclonal antibody, tumors did not develop appreciably beyond the palpable size of day 1. In contrast, control animals exhibited exponential growth of tumors. Comparison of the two different groups revealed approximately a 600% reduction in tumor growth in the antibody treated animals as compared to the controls. Further, no visible signs of monoclonal antibody toxicity in the treated animals were observed. There was no change in animal weight before and after antibody treatment. Tissues including heart, lung, liver, kidney, spleen, brain, pancreas and intestine appeared normal in control and antibody-treated animals.

Taken together, these experiments demonstrate annexin II to be the physiologic receptor for angiostatin and to play a central role in angiogenic processes, including those involved in tumor growth.

Accordingly, the present invention provides methods for identifying compositions that inhibit angiogenesis though their interaction with annexin II and/or angiostatin. Further, the present invention relates to methods of using these composition in the inhibition of angiogenesis and in the induction of apoptotic activity of endothelial cells. Such compositions are thus useful in the treatment of various diseases or disorders associated with unwanted angiogenesis including, but not limited to, cancer, macular degeneration, diabetic retinopathy and rheumatoid arthritis.

Exemplary compounds useful in inhibiting angiogenesis and inducing apoptosis in endothelial cells based upon their interaction with annexin II and/or angiostatin include, but are not limited to, antibodies against annexin II, soluble forms of annexin II, peptides or peptide fragments which mimic one or more of the 4 kringle domains which comprise angiostatin, and small organic molecules which bind to annexin II, and immunogenic forms of annexin II which are capable of inducing antibody production against annexin. In one embodiment of the present invention, the immunogenic annexin II is administered as a vaccine to invoke an immune response against annexin II, thereby inhibiting unwanted angiogenesis such as occurs in tumors. Methods for rendering a protein such as annexin II immunogenic are well known in the art and can be performed routinely by the skilled artisan. Also well known are methods of formulating vaccines from immunogenic proteins.

For purposes of the present invention, by the term "antibody" it is meant to include polyclonal, monoclonal, omniclonal antibodies, and antibodies prepared via molecular biology techniques, as well as antibody fragments and aptamers and single-stranded oligonucleotides such as those derived from an in vitro evolution protocol referred to as SELEX and well known to those skilled in the art. The term "antibody" as used herein is also meant to be inclusive of chimeric, single chain, and humanized antibodies, as well as Fab fragments, or the product of an Fab expression library. Various procedures known in the art may be used for the production of such antibodies.

Other compounds for use in the present invention which interact with annexin II and/or angiostatin can be identified routinely by those of skill in the art based upon the teachings provided herein. In one embodiment, compounds can be screened to determine their ability to bind to annexin II receptors. Compounds identified with the ability to bind to annexin II receptors can then be tested in additional assays to examine their anti-angiogenic assay and their ability to induce apoptosis in endothelial cells. More preferably, compounds for use in the present invention can be screened for their ability to compete with angiostatin for binding to annexin II. Compounds which displace angiostatin or compete effectively with angiostatin for binding to annexin II are expected to mimic the anti-angiogenic activity and the ability to induce apoptosis in endothelial cells.

Endothelial cells can then be contacted with an effective amount of a compound which binds to annexin II to inhibit angiogenesis in the endothelial cells and to selectively induce apoptosis in the endothelial cells. By "effective amount" it is meant a concentration of compound which is capable of inhibiting angiogenesis and selectively inducing cell death of the endothelial cells. Such concentrations can be determined routinely by those of skill in the art based upon activity of the compound in in vitro assays such as described herein as well as angiogenic assays well known in the art. Various routes of administration can be used including, but not limited, oral, intravenous, topical, intra tumoral, and intramuscular or subcutaneous, and selection will depend upon the pharmacokinetic properties, the bioavailability of the compound to be administered and the condition being treated.

In a preferred embodiment, the compound is incorporated into a pharmaceutical composition also comprising a pharmaceutically acceptable vehicle. In this embodiment, it is preferred that the compound compete with angiostatin for binding to annexin II. Appropriate pharmaceutically acceptable vehicles can be selected routinely by one of skill in the art based upon the solubility of the compound and the route by which the compound is being administered.

The following non-limiting examples are presented to better illustrate the present invention.

EXAMPLES

Example 1

Angiostatin Generation and Purification

Angiostatin was generated by limited proteolytic digestion of human plasminogen using purified bovine pancreatic elastase as described by O'Reilly et al. (1994. *Cell* 79:315-328). In a typical reaction, plasminogen was cleaved into two fragments of about 38 and 19 kDa, which were recognized by anti-K1-3 monoclonal antibody. The elastase digestion mixture was applied onto a lysine Sepharose column. The loaded column was washed extensively with 10 column volumes of phosphate-buffered saline (PBS), which removed elastase and other unabsorbed proteins. The column was further washed with 5 column volumes of 100 mM NaCl to remove low affinity bound proteins. The high affinity lysine binding fragment was specifically eluted with 200 mM ε-amino capric acid (ACA) in 100 mM NaCl. All the fractions were analyzed on SDS-PAGE and stained with Coumassie as well as with silver and further confirmed by Western blot analysis to check for purity and homogeneity. The homogeneous fractions cross-reacting with anti-plasminogen antibodies were pooled together, concentrated by pressure dialysis, and extensively dialyzed against 1 liter of PBS for three days with five changes of buffer. The final preparation was sterilized by passage through 0.22 micron filter, aliquoted and stored at −70° C.

Example 2

Cell Culture

Bovine aortic endothelial cells (BAEC) and human umbilical cord vein endothelial cells (HUVEC) were maintained in Ham's F-12 K medium (Sigma Chemical Co.) Supplemented with 1% glutamine, 10% FBS, 50 U/ml penicillin, 50 μg streptomycin, and 50 μg/ml gentamycin. To identify angiostatin binding proteins, cells were scraped with a rubber policeman and washed 3 times with chilled PBS before homogenizing. Fibroblast cells were cultured in DMEM containing 10% FBS and antibiotics.

Example 3

Endothelial Cell Proliferation Assay

Bioactivity of angiostatin was characterized by inhibition of endothelial cell proliferation. Bovine aortic endothelial cells (BAEC) were obtained and grown as described previously (Qian, X. et al. 1997. *Exp. Cell Res.* 235:403-412). For the proliferation assays, cells were washed with PBS an dispersed by treatment with a 0.05% trypsin solution. Cells were then plated in 96 well culture plates containing 2% FBS in Ham's F12-K medium at a density of 10,000 cells/well for 24 hours at 37° C. Media was then replaced with Ham's F-12 K containing 0.1% BSA and cells further grown for 24 hours to synchronize the culture. After 24 hours, different concentrations of angiostatin were added, and 20 minutes later bFGF (1 ng/ml) was added. The cultures were incubated for 36 hours. The cells treated with bFGF alone were considered as 100% activity. Viability of control and treated cells was measured with a calorimetric cell proliferation assay kit from Promega. This assay determines the metabolic activity of live cells by a dehydrogenase enzyme which converts Owen's reagent into soluble formazan.

Example 4

Ligand Immunoblot Assay

BAEC lysate was prepared by either homogenization of cells with a Dounce homogenizer or by sonication. Total protein concentration was determined. Endothelial cell proteins were separated by 12% SDS-PAGE. Resolved proteins were transferred to a nitrocellulose membrane at constant voltage of 100 V for one hour. The membrane was washed and blocked for one hour in 5% nonfat dry milk at room temperature. Membranes were then incubated overnight at 4° C. with angiostatin at 1 μg/ml. After extensive washing with Trisbuffered saline containing 0.2% Tween 20 (TBST), the membrane was re-incubated with anti-Kringle 1-3 (K1-3) monoclonal antibody at a dilution of 1:100 for one hour at room temperature. The blot was developed using HRP-labeled anti-mouse IgG and enhanced chemiluminescence according to manufacturer's instructions. Angiostatin was included as a positive control in the first lane of the gel to ensure accuracy and validity.

Example 5

Solid Phase Radioligand Binding Studies

Angiostatin and plasminogen ligands were radioiodinated to a specific activity of $5.2 \times 10^6$ cpm/μg and $6.6 \times 10^6$ cpm/μg, respectively, using iodobeads (Pierce, Rockford, Ill.) and labeled angiostatin and plasminogen were further purified by gel filtration. Unbound radiolabeled iodine was removed by dialysis against PBS, pH 7.4, and the purity of labeled angiostatin and plasminogen was checked by SDS-PAGE before the ligands were used in binding studies. Plastic plates were coated with 100 ng of annexin II in PBS by shaking at room temperature for 24 hours. The annexin II immobilized plates were blocked with 1% BSA in PBS for 1 hour. Annexin II coated plates were incubated with 1 μM $^{125}$I-labeled angiostatin and plasminogen in 100 μl PBS for 3-4 hours with continuous shaking. After incubation, wells were washed with TBST and remaining radioactivity was quantified by gamma counting. Nonspecific binding was measured in the presence of 1% BSA.

Example 6

Kinetic Analysis of Angiostatin Binding to Immobilized Annexin II

Anti-annexin II monoclonal antibody (40 μg) was incubated with 40 μg of purified annexin II in a reaction volume of 200 μl with PBS for one hour at 4° C. One ml of Protein A Sepharose was added overnight to the reaction mixture with gentle shaking. More than 98% anti-annexin II antibody and annexin II complex bound to Protein A Sepharose as determined by SDS-PAGE. Protein A Sepharose gel was centrifuged at 2000-3000 rpm for 5 minutes. Supernatants were removed and the gels washed 3-4 times to remove any unbound proteins. Protein A Sepharose gel was incubated with 0.1% BSA for 1 hour to block the non-specific binding sites. BSA was removed by centrifugation and the gels washed and re-suspended in PBS. The annexin-II immobilized gels (10 μl) were incubated with increasing concentrations of $^{125}$I-angiostatin in a final volume of 100 μl. Non-specific binding was determined in parallel experiments using only anti-annexin II antibody immobilized to a Protein A Sepharose gel. Following incubation, gels were separated by centrifugation at 3000 rpm for 5 minutes after which the supernatant was removed and gels then washed rapidly 3-4 times with PBS to remove non-specifically bound material. The amount of bound radiolabeled angiostatin was calculated based on the level of radioactivity present in the gels.

Example 7

Determination of the Binding Specificity

To characterize binding specificity, a 100-fold molar excess of unlabeled ligand was incubated for 30 minutes before adding the $^{125}$I-angiostatin of $^{125}$I-plasminogen. The gel-associated radioactivity was quantified via an LKB γ radiation counter. To characterize protein bound to immobilized annexin II, gels were suspended in 25 γl of SDS sample buffer and eluted proteins separated on 12% SDS-PAGE, gels dried and processed for autoradiography.

Example 8

Binding to Endothelial Cells

BAEC were plated in 96 well culture plates suspended in Ham's F12 K medium containing 2% FBS at a density of 10,000 cells/well. Media was then replaced with Ham's F12 K containing 0.1% BSA and cells were further grown for 24 hours to synchronize the culture. After 24 hours, cells were washed and incubated with 1 μM $^{125}$I-angiostatin or $^{125}$I-plasminogen in a total volume of 100 μl binding buffer (PBS containing 3 mM $CaCl_2$, 1 mM $MgCl_2$, and 5 mg/ml BSA) for 45 minutes at 4° C. with gentle shaking. Empty wells treated in parallel were used as controls. After incubation, cells were rapidly washed 5 times to remove non-specifically bound material. The cells were solubilized in 1% SDS, 0.5 M NaOH, 0.01 M EDTA. Aliquots were transferred to counting vials and counted in a gamma counter. Non-specific counts were subtracted form the total counts bound. The data were analyzed using non-linear curve fitting and Michaelis-Menton kinetics with Prizm software (San Diego, Calif.).

Example 9

Ligand Immunoprecipitation

Purified angiostatin and annexin II were incubated 2 to 3 hours at 4° C. with gentle shaking. The complex was then allowed to bind with anti-annexin II monoclonal antibody at 4° C. for 3 to 4 hours. This tri-molecular complex was immobilized on Protein A Sepharose gel at 4° C. overnight. The gel was centrifuged and washed to remove any unbound protein. The gel was suspended in 50 μl SDS loading buffer and heated to 37° C. for 10 to 15 minutes and then separated by centrifugation. The eluted protein was then loaded on a 12% SDS-PAGE gel and separated at 100 V. The gel was electroblotted to a nitrocellulose membrane and probed with an anti-kringle 1-3 antibody followed by an HRP-conjugated secondary antibody and developed by electrochemiluminescence.

Example 10

Immunocytochemistry

Immunocytochemistry was performed on BAEC cultured in 4 chamber tissue culture slides. Cells were fixed and permeabilized with 95% ethanol and incubated with angiostatin (1 μg/ml) for 2 hours and washed extensively with PBS and then re-incubated with anti-kringle 1-3 monoclonal antibody for 1 hour (1:100). Control cells were incubated with either angiostatin or antibody alone. Staining was performed using the appropriate conjugated secondary antibody followed by treatment with HRP avidin biotin as previously described (Tuszynski, G. P. and R. F. Nicosia. 1994. *Lab. Invest.* 70:228-233). Cells were counterstained with hematoxylin and photomicrographed under bright field microscopy.

Example 11

Purification of Angiostatin Receptor

Large scale (approximately 100 roller bottles) of mycoplasma-free BAEC were cultured in the National Cell Culture facility (Cellex Biosciences, Minneapolis, Minn.). A packed cell volume of endothelial cells (15 ml) were washed in chilled PBS and homogenized in chilled Tris-sucrose buffer, pH 7.4, containing the protease inhibitors leupeptin (4.2 μM), anti-pain (3.3 μM), and phenylmethylsulfonylfluoride (0.57 mM) and fractionated according to the method of Sharma and Shapiro (1995. *Arch. Riochem. Biophys.* 316:478-484). The ultracentrifuged purified microsomal plasma membrane fraction was solubilized in homogenizing buffer and stored at 4° C. for further purification. Before starting the purification, all fractions were checked for angiostatin binding by ligand blot analysis. The annexin II fraction was solubilized by dropwise addition of 0.5% Triton X-100 lysis buffer containing protease inhibitors. The solubilized membrane fraction was further centrifuged at 105,000×g for 30 minutes to remove any insoluble material. The supernatant was extensively dialyzed against buffer A (10 mM Tris-HCl, pH 7.4, 0.1 mM dithiothreitol, 0.1% cholamidopropyldimethyl ammonio-1-propane sulphonate, 1 mM EDTA, and 5% glycerol for 2 days to remove all residual Triton X-100.

All further purification was performed at 4° C. unless otherwise noted. The dialysate derived from the solubilized microsomal plasma membranes was applied to a Fractogel strong anion exchange column (2.5 20 cm) at a flow rate of 0.2 ml/minute previously equilibrated with 10 column volumes of buffer A. After sample application, the column was first washed with 10 column volumes of buffer A until the absorbance at 280 nm was between 0-0.050 absorbance units. The column was eluted with a linear gradient of 0-1 M KCl in buffer B. Eluates from the column were monitored at 280 nm and peaks were analyzed for angiostatin binding protein (annexin II) by ligand binding. Fractions enriched for angiostatin binding were pooled, concentrated by pressure dialysis and dialyzed overnight with four changes against 10 mM Tris-HCl, pH 7.4 containing 5% glycerol, 1 mM EDTA, 1 mM dithiothreitol. The dialyzed fraction was further chromatographed on a hydroxylapatite column followed by angiostatin affinity chromatography. Proteins were eluted by a linear gradient of 1 to 100% of buffer A-B, respectively. Eluates from the column were monitored at 280 nm and peaks were analyzed by angiostatin ligand blot analysis. Binding fractions were pooled, concentrated and dialyzed against 10 mM potassium phosphate buffer, pH 7.4, containing 0.1 mM dithiothreitol and 0.1 mM EDTA. Purity of the dialyzed fraction was determined by SDS-PAGE. The gel was stained with Coumassie blue as well as silver to detect any slight contamination. Any contaminating proteins were removed by angiostatin affinity chromatography. The final homogeneous protein product was characterized by angiostatin ligand blot analysis and then the protein was stored at -80° C.

Example 12

Protein Microsequencing

Approximately 30 pmoles of the purified endothelial protein was resolved on SDS-PAGE and stained with Coumassie blue. The protein band was excised from the gel and subjected to tryptic digestion. The resultant peptide fragments were separated by high performance liquid chromatography (HPLC) and further characterized by mass spectrometry. Three fragments were sequenced by Edman degradation.

What is claimed is:

1. A method for treating cancer comprising administering to a patient an effective amount of a compound which competes with angiostatin for binding to annexin II, wherein the compound comprises an antibody specific for annexin II.

* * * * *